(12) United States Patent
Knops et al.

(10) Patent No.: US 6,476,274 B1
(45) Date of Patent: Nov. 5, 2002

(54) METHOD OF PRODUCING CYCLOBUTANONE

(75) Inventors: Hans-Joachim Knops, Monheim (DE); Bernd Gallenkamp, Wuppertal (DE); Lubbertus Mulder, Hagen (DE); Stefan Antons, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/936,121

(22) PCT Filed: Mar. 1, 2000

(86) PCT No.: PCT/EP00/01707

§ 371 (c)(1), (2), (4) Date: Sep. 6, 2001

(87) PCT Pub. No.: WO00/53553

PCT Pub. Date: Sep. 14, 2000

(30) Foreign Application Priority Data

Mar. 10, 1999 (DE) .......................................... 199 10 464

(51) Int. Cl.[7] .......................... C07C 45/29; C07C 45/32
(52) U.S. Cl. ........................ 568/342; 568/354; 568/361; 568/364; 568/397; 568/402
(58) Field of Search ................................. 568/342, 354, 568/361, 364, 397, 402, 839

(56) References Cited

PUBLICATIONS

React. Funct. Polym., 29 (2), (month unavailable) 1996, pp. 101–114, Anja M.J. Jorna, Alexandra E.M. Boelrijk, Hans J. Hoorn, Jan Reedijk, Heterogenization of a ruthenium catalyst on silica and its application in alcohol oxidation and stilbene epoxidation.

Can. J. Chem., 62 (9), Mar. 20, 1984, pp. 1835–1839, Donald G. Lee, Ligaya N. Congson, Udo A. Spitzer amd Merle E. Olson, The oxidation of alcohols by sodium ruthenate.

Org. Synth., 60 (month unavailable) 1981, pp. 20–25, Cyclobutanone.

JACS, 96(21) Oct. 16, 1974, pp. 6647–6657, Kenneth B. Wiberg and Samir K. Mukherjec, Chromic Acid Oxidation of Cyclobutanol.

*Coleman, K. et al: "Selective Catalystic Oxidation of Alcohols by Ruthenium–copper Bifunctional System Using Molecular Oxygen", Eur. J. Inorg. Chem., vol. 11, 1998, pp. 1673–1675, XP000909457.

*Anon.: "A process for making diketon from diol" Research Disclosure, No. 380, 1995, pp. 816–820, XP000549835.

Primary Examiner—James O. Wilson
Assistant Examiner—Sikarl A. Witherspoon
(74) Attorney, Agent, or Firm—Joseph C. Gil; Richard E. L. Henderson

(57) ABSTRACT

The invention relates to a process for preparing cyclobutanone by oxidizing cyclobutanol with an alkali metal hypochlorite or alkaline earth metal hypochlorite in the presence of an acid.

5 Claims, No Drawings

METHOD OF PRODUCING CYCLOBUTANONE

The invention relates to a novel process for preparing cyclobutanone.

It is known that cyclobutanone is obtained by oxidation of cyclobutanol. The processes which have been described employ customary organic oxidants such as various dialkyldioxiranes, chloral, tert-butyl hydroperoxide or substituted or unsubstituted perbenzoic acids; or transition metal or noble metal catalysts including their oxides and oxide complexes (cf., for example, React. Funct. Polym., 29 (2), 101–14, 1996; Can. J. Chem., 62 (9), 1835–9, 1984; Org. Synth., 60, 20–5, 1981; and JACS, 96 (21), 6647–57, 1974).

For an industrial-scale process, the systems chromium (VI) oxide/oxalic acid and ruthenium oxide/sodium periodate are also possible from a process engineering point of view. However, these have the general disadvantage of an excessively high cost of the catalyst system (in the case of ruthenium oxide) or the large amounts of waste and their disposal (in the case of chromium and iodine).

Further known common nonoxidative methods of preparation, e.g. photodecomposition, photooxidation or cyclization, with or without subsequent hydrolysis of derivatives of carbonyl functions, are only suitable on a laboratory scale.

It has been found that cyclobutanone is obtained when cyclobutanol is oxidized by means of alkali metal hypochlorite or alkaline earth metal hypochlorite in the presence of an organic or inorganic acid as solvent.

The process of the present invention surprisingly makes it possible to obtain cyclobutanone in a simple manner in very good yields and in high purity without the cyclobutane ring being expanded to butyrolactone in a BAYER-VILLIGER oxidation as main reaction and opened.

The reaction according to the invention thus has the advantage of a simple, inexpensive and environmentally friendly method of obtaining cyclobutanone, in particular on an industrial scale.

If, for example, the system aqueous sodium hypochlorite/acetic acid is used for the oxidation, the reaction in the process of the invention can be represented by the following scheme:

Cyclobutanol as starting material is a generally known compound in organic chemistry and is obtainable in a generally known manner, e.g. by reaction/ring expansion of cyclopropyl carbinol with concentrated hydrochloric acid (cf., for example, Org. Synth. 60, 20–25, 1981).

Preferred alkali metal and alkaline earth metal hypochlorites are sodium, potassium and calcium hypochlorites. The hypochlorites are usually used as aqueous solutions. The technical-grade solutions are generally suitable.

Preferred organic acids are alkanoic acids, in particular $C_1$–$C_4$-alkanoic acids such as acetic acid; preferred inorganic acids are mineral acids, in particular hydrochloric acid.

The aqueous sodium hypochlorite/glacial acetic acid system is particularly advantageous.

The reaction temperatures in the oxidation can be varied within a wide range. In general, the oxidation is carried out at from −20° C. to +30° C., preferably from −20° C. to +20° C., particularly preferably from −10° C. to +10° C.

The work-up is carried out in a customary fashion; the pH may optionally be kept in the slightly basic range by addition of alkali metal carbonate or alkali metal hydrogencarbonate, in particular potassium hydrogencarbonate or sodium hydrogencarbonate (cf. the preparative examples).

In one particular embodiment of the process of the invention the starting material cyclobutanol can be prepared from cyclopropyl carbinol in the presence of acids, especially concentrated mineral acids, and the subsequent oxidation to cyclobutanone can be conducted in a kind of "one-pot" reaction, i.e. in situ without isolating the intermediate or changing the solvent (of the preparative examples).

The preparation of cyclobutanol from cyclopropyl carbinol is known per se. It is generally carried out in water as solvent in the presence of acids, in particular mineral acids such as concentrated hydrochloric acid. Typical reaction temperatures are in the range from 20° C. to 120° C.; the reaction is generally carried out under reflux conditions.

The cyclobutanone to be prepared by the process of the invention represents a key intermediate of general interest.

PREPARATIVE EXAMPLES

Example 1

6.3 kg (76.1 mol; 84% pure) of cyclobutanol are dissolved in 23.6 l of acetic acid while stirring and the solution is metered into 42 l of aqueous sodium hypochlorite (13% active chlorine) at 0° C. to 5° C. (jacket temperature: −18° C.) over a period of 5 hours. The yellowish suspension is stirred for 12 hours (overnight) at from 3° C. to 10° C. and subsequently stirred into 87 l of water, resulting in a pH of 3.

The mixture is extracted with 2×30 l and 2×16 l of methylene chloride, resulting in the aqueous phase becoming clear. The organic phase is stirred into 60 l of water, after which 6.9 kg of sodium hydrogencarbonate are slowly (foaming!) added while stirring, resulting in a pH of 6. The aqueous phase is separated off, the organic phase is admixed with 30 l of water, followed by addition of another 2.3 kg of sodium hydrogencarbonate while stirring, bringing the pH to 8.

The organic phase is separated off and evaporated at 40° C. and 550–600 mbar in a vessel. The residue (18.2 kg) is fractionally distilled in the distillation laboratory.

This gives 3.52 kg (64.75% of theory) of cyclobutanone having a boiling point of 88° C./1750 mbar and a purity of 98% according to GC.

Example 2

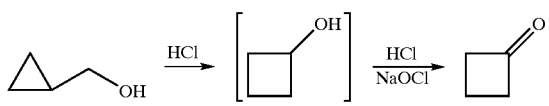

73.1 g (1 mol) of cyclopropyl carbinol in 680 ml of water are admixed with 100 ml of concentrated hydrochloric acid and refluxed for 3 hours. 819 g of aqueous sodium hypochlorite (13% active chlorine) are subsequently added dropwise to the reaction mixture at from 0° C. to 5° C. over a period of 3 hours, with the pH being kept at not more than 2 (addition of hydrochloric acid if necessary). The mixture is stirred further for about 4 hours at from 0° C. to 5° C. and is extracted twice with 250 ml each time of dichloromethane. The combined extracts are evaporated by distilling off the solvent and the residue is distilled under atmospheric pressure.

This gives 59.4 g (84.7% of theory) of cyclobutanone having a purity of 95.5% according to GC.

What is claimed is:

1. A process for preparing cyclobutanone comprising oxidizing cyclobutanol with an alkali metal hypochlorite or alkaline earth metal hypochlorite in the presence of an acid.

2. A process according to claim 1 wherein the acid is a $C_1$–$C_4$-alkanoic acid.

3. A process according to claim 1 wherein the alkali metal hypochlorite is sodium hypochlorite.

4. A process according to claim 1 wherein the oxidation is carried out at a temperature of from −20° C. to +30° C.

5. A process according to claim 1 wherein the cyclobutanol is prepared by rearrangement of cyclopropyl carbinol in the presence of an acid and then oxidized in situ to form cyclobutanone.

* * * * *